US009730952B2

(12) United States Patent
Bombardelli et al.

(10) Patent No.: US 9,730,952 B2
(45) Date of Patent: Aug. 15, 2017

(54) METHODS FOR TREATING AND PREVENTING MUCOSITIS

(75) Inventors: Ezio Bombardelli, Groppello Cairoli (IT); Paolo Morazzoni, Milan (IT)

(73) Assignee: Indena S.p.A., Milan (IT)

( * ) Notice: Subject to any disclaimer, the term of this patent is extended or adjusted under 35 U.S.C. 154(b) by 1605 days.

(21) Appl. No.: 12/856,786

(22) Filed: Aug. 16, 2010

(65) Prior Publication Data

US 2010/0310684 A1    Dec. 9, 2010

Related U.S. Application Data

(63) Continuation of application No. 11/829,138, filed on Jul. 27, 2007, now abandoned.

(30) Foreign Application Priority Data

Jul. 28, 2006 (EP) .................................... 06015732

(51) Int. Cl.
A61K 36/28 (2006.01)
A61K 36/45 (2006.01)
A61K 36/66 (2006.01)
A61K 31/7048 (2006.01)
A61K 31/352 (2006.01)
A61K 36/51 (2006.01)

(52) U.S. Cl.
CPC ........ *A61K 31/7048* (2013.01); *A61K 31/352* (2013.01); *A61K 36/28* (2013.01); *A61K 36/45* (2013.01); *A61K 36/51* (2013.01); *A61K 36/66* (2013.01)

(58) Field of Classification Search
None
See application file for complete search history.

(56) References Cited

U.S. PATENT DOCUMENTS

| | | | |
|---|---|---|---|
| 4,145,412 | A | 3/1979 | Ladanyi |
| 4,818,533 | A | 4/1989 | Boulware et al. |
| 5,200,186 | A | 4/1993 | Gabetta et al. |
| 5,378,465 | A | 1/1995 | Zeines |
| 5,665,365 | A | 9/1997 | Bombardelli et al. |
| 5,840,322 | A | 11/1998 | Weiss et al. |
| 6,162,393 | A | 12/2000 | De Bruiju et al. |
| 6,706,256 | B2 | 3/2004 | Lawlor |
| 2006/0263455 | A1 | 11/2006 | Anton |
| 2008/0145319 | A1 | 6/2008 | Bombardelli et al. |

FOREIGN PATENT DOCUMENTS

| | | | |
|---|---|---|---|
| EP | 0464298 A1 | 1/1992 | |
| EP | 1 236 466 | 9/2002 | |
| FR | 2856304 A | 12/2004 | |
| GB | 2 396811 | 7/2004 | |
| IT | MI20042414 A1 * | 3/2005 | ............ A61K 36/66 |
| JP | 2001039844 | 2/2001 | |
| WO | WO 96/11692 | 4/1996 | |
| WO | WO 97/41137 | 11/1997 | |
| WO | WO 00/02570 | 1/2000 | |
| WO | WO 01/15553 A1 | 3/2001 | |
| WO | WO 02/094300 A1 | 11/2002 | |
| WO | WO 03/013428 A2 | 2/2003 | |
| WO | WO 03/039452 A2 | 5/2003 | |
| WO | WO 03/088986 A1 | 10/2003 | |
| WO | WO 2005/053719 A2 | 6/2005 | |
| WO | WO 2006/024545 | 3/2006 | |
| WO | WO 2006/063716 A1 | 6/2006 | |
| WO | WO 2006/071342 A2 | 7/2006 | |
| WO | WO 2007/038421 A2 | 4/2007 | |
| WO | WO 2007/073518 A2 | 6/2007 | |

OTHER PUBLICATIONS

Goodman and Gilman's the Pharmacological Basis of Therapeutics. editors Joel G. Hardman and Lee E. Limbird, published by the McGraw-Hill Companies, Inc., 2001, p. 5-8.*
"Mucositis (Mouth Sores) & Oral Care Tip Sheet" by OncoLink [online]. Retrieved on Mar. 20, 2013. Retrieved from the internet at <http://www.oncolink.org/includes/print_article.cfm?Page=2 &id=966&Section=Coping_With_Cancer&pdf=1>.*
Third Party Submission under 37 C.F.R. § 1.99 dated Jan. 22, 2011 in connection with U.S. Appl. No. 12/856,786, filed Aug. 16, 2010. Represented in reference C20 above to be Abu Ali Ibn-e-Sina; Al-Qaanoon-fil-Tibb, vol. II ($11^{th}$ Century AD), Institute of History of Medicine and Medicinal Research, Jamia Hamdard, New Delhi 62, 1987 AD; pp. 340-341; and what was represented in reference C20 above to be an English translation including Terminology Conversion (TKDL Extract).
Represented in reference C20 above to be Abu Bakr Mohammad. Bin Zakariyya Al-Razi; Kitaab-al-Haawi-fil-Tibb, vol. III ($9^{th}$ century AD), Dayerah-al-Ma'aarif Usmania, Hyderabad, (Second Edition) 1977 AD; p. 307; and what was represented in reference C20 above to be an English translation including Terminology Conversion (TKDL Extract).
Represented in reference C20 above to be Abu Bakr Mohammad. Bin Zakariyya Al-Razi; Kitaab-al-Haawi-fil-Tibb, vol. III ($91^{th}$ century AD), Dayerah-al-Ma'aarif Usmania, Hyderabad, (Second Edition) 1977 AD; p. 309; and what was represented in reference C20 above to be an English translation including Terminology Conversion (TKDL Extract).

(Continued)

*Primary Examiner* — Leigh C Maier
(74) *Attorney, Agent, or Firm* — Jones Day

(57) ABSTRACT

Methods for treating and preventing mucositis, in particular mucositis following the administration of chemotherapy drugs or a combination of said drugs with radiotherapy, are disclosed herein. More specifically, disclosed herein is the administration of a therapeutically effective amount of at least one of an anthocyanoside, a proanthocyanidin, or an extract containing at least one of an anthocyanoside or a proanthocyanidin for the treatment or prevention of mucositis. The therapeutically effective amount of the anthocyanoside, proanthocyanidin or extract can be administered alone or in combination with a therapeutically effective amount of at least one of an anti-inflammatory agent, immunomodulating agent, analgesic, antimicrobial agent or antifungal agent. Also disclosed herein are pharmaceutical compositions for treating and preventing mucositis.

11 Claims, No Drawings

(56) References Cited

OTHER PUBLICATIONS

Represented in reference C20 above to be Mohammad Azam Khan; Muheet-e-Azam vol. III (19$^{th}$ century AD), Matba Nizami, Kanpur, 1887 AD; p. 105; and what was represented in reference C20 above to be an English translation including Terminology Conversion (TKDL Extract).

Represented in reference C20 above to be Lankapatiravana; Arkaprakasah-Edited and translation by Indradeva Tripathi; Krishnadas Academy, Varanasi, Edn. 1$^{st}$ 1995; p. 119; and what was represented in reference C20 above to be an English translation including Terminology Conversion (TKDL Extract).

Represented in reference C20 above to be Bharata Bhaisajya Ratnakara—Compiled by Naginadasa Chaganalala Saha, Translated by Gopinath Gupta—vol. III: B. Jain Publishers, New Delhi, Edn, 2$^{nd}$ Reprint, Aug. 1999; [This book contains back references from 1000 B.C. to 20$^{th}$ century]; p. 18; and what was represented in reference C20 above to be an English translation including Terminology Conversion (TKDL Extract).

Represented in reference C20 above to be Vagabhata; Astanga Hrdaya—(commentary by Arunadutta) edited by Bhisagacarya Harisastri Paradakara vaidya: Chaukhamba Orientalia, Varanasi, edn 8$^{th}$, 1998; [Time of origin 5$^{th}$ century]; p. 855; and what was represented in reference C20 above to be an English translation including Terminology Conversion (TKDL Extract).

Represented in reference C20 above to be Abdulla Sahib; Anuboga Vaithiya Navaneetham, Pub: Palani Thandayuthapani Devasthanam publications, Directorate of Indian systems of Medicine, Chennai. (1975); p. 109; and what was represented in reference C20 above to be an English translation including Terminology Conversion (TKDL Extract).

Represented in reference C20 above to be Agasthiyar: Agathiyar vaithya vallathi 600, Pub & Ed Deenadhayalu muthaliar, Chennai, (1924); pp. 88, 89; and what was represented in reference C20 above to be an English translation including Terminology Conversion (TKDL Extract).

Represented in reference C20 above to be Mohammad Akmal Khan; Qaraabaadeen Azam wa Akmal (20$^{th}$ century AD), Matba Siddiqi, Delhi/Marba Mustafai, Delhi, 1909 AD; p. 166; and what was represented in reference C20 above to be an English translation including Terminology Conversion (TKDL Extract).

Chaturvedi et al., "Sanguinarine (Pseudochelerythrine) is a Potent Inhibitor of NF-kappaB Activation, IkappaBalpha Phosphorylation, and Degradation," *J. Bio. Chem.* 272(48), pp. 30129-30134 (1997) (XP002378504).

Cheminat et al., "Cyanidin 3-malonylglucoside in Two *Echinacea* Species," *Phytochem* 28(11), pp. 3246-3247 (XP002378500).

Database WPI, Section Ch, Week 200313, Derwent Publications Ltd. London, GB; Class B04, AN 2003-137579, KR 2002 073 025 A (Lee Y C) (2002) Abstract (XP002378506).

International Preliminary Report on Patentability dated Jun. 19, 2007 for PCT/EP2005/013047, filed Dec. 6, 2005.

International Search Report mailed May 15, 2006 for PCT/EP2005/013047, filed Dec. 6, 2005.

Jayaprakasha et al., "Antibacterial and Antioxidant Activities of Grape (*Vitis vinifera*) Seed Extracts," *Food Res International*, 36, pp. 117-122 (2003) (XP002378501).

Knox et al., "Activity of Anthocyanins From Fruit Extract of *Ribes nigrum* L. Against Influenza A and B Viruses," *Acta Virgologica*, 45, pp. 209-215 (2001) (XP 009065720).

Non-final Office Action mailed Dec. 22, 2010 for U.S. Appl. No. 11/793,089, filed Jan. 31, 2008.

Schlesinger et al., "Effect of Cranberry Juice Constituents on Haeamgglutination and Infectivity of Influenza Virus," *Antiviral Res.* 57(3): A82 Abstract 140 ( 2003) (XP002378502).

Written Opinion of the International Searching Authority dated May 15, 2006 for PCT/EP2005/013047, filed Dec. 6, 2005.

Bruyere et al. "Utilisation de la canneberge dans les infections urinaires recidivantes, use of cranberry in chronic urinary tract infections", Medecine et maladies infectieuses, vol. 36; pp. 358-363 (2006) (English Abstract Included).

European Search Report for Application No. 06015732.8-1216 mailed Feb. 27, 2007.

European Search Report for Application No. 12177486.3-1216 mailed Oct. 5, 2012.

European Search Report for Application No. 12177483.0-1216 mailed Oct. 15, 2012.

International Preliminary Report on Patentability dated Feb. 3, 2009 for PCT/IB2007/002147, filed Jul. 27, 2007.

Martin et al. The effects of resveratrol, a phytoalexin derived from red wines, on chronic inflammation induced in an experimentally induced colitis model, British J. Pharma., vol. 147(8); pp. 873-885 (2006).

Communication for European Patent Application No. 07 804 655.4, mailed Jul. 14, 2010.

Third Party observations submitted to the European Patent Office mailed Jun. 29, 2010 for European Patent Application No. 07804655.4-1216.

Yoshikazu et al., "The protective and hormonal effects of proanthocyanidin against gastric mucosal injury in Wistar rats", J. Gastro. vol. 39. pp. 831-837 (2004).

Barasch et al., Antimicrobials, mucosal coating agents, anesthetics, analgesics, and nutritional supplements for alimentary tract mucositis. *Support Care Cancer*, vol. 14, pp. 528-532 (2006).

Blumenthal Ed., The Complete German Commission E Monographs: Therapeutic Guide to Herbal Medicines, First Edition, p. 88 (1998).

Choi et al., "Protective effect of anthocyanin-rich extract from bilberry (*Vaccinium myrtillus* L.) against myelotoxicity induced by 5-fluorouracil," *BioFactors* 29, pp. 55-65 (2007).

Definition of "prevent" from the Merriam Webster Online Dictionary [online], [Retrieved on Aug. 15, 2008]. Retrieved from the internet http://merriam-webster.com/cgi-bin/dictionary?book=Dictionary&va=prevent.

Donnelly et al., "Antimicrobial therapy to prevent or treat oral mucositis," *The Lancet*, vol. 3, pp. 405-412 (2003).

European Search Report dated Feb. 27, 2007 for European Patent Application Serial No. 06015732.8-1216.

Godowski, "Antimicrobial Action of Sanguinarine," *J. Clin. Dentistry*, vol. 1:4, pp. 96-101 (1989).

Hou et al., "Anthocyanidins inhibit cyclooxygenase-2 expression in LPS-evoked macrophages: Structure-activity relationship and molecular mechanisms involved," *Biochemical Pharma.*, vol. 70, pp. 417-425 (2005).

International Search Report mailed Jul. 16, 2008 for PCT/IB2007/002147, filed Jul. 27, 2007.

Magistretti et al., "Antiulcer activity of an anthocyanidin from vaccinium myrtillus," *Arzneimittel Forschung: Drug Research*, vol. 38:1 nr. 5, pp. 686-690 (1988).

Matsumoto et al., "Gastroprotective effect of red pigments in black chokeberry fruit (*Aronia melanocarpa* Elliot) on acute gastric hemorrhagic lesions in rats," *J Agric. Food Chem.*, vol. 52, pp. 2226-2229 (2004).

Moroni et al., Possible efficacy of allopurinol vaginal washings in the treatment of chemotherapy-induced vaginitis, *Cancer Chemo. and Pharma.*, vol. 41, pp. 171-172 (1997).

Non-final Office Action mailed Jun. 5, 2009 for U.S. Appl. No. 11/829,138, filed Jul. 27, 2007.

Non-final Office Action mailed Feb. 17, 2010 for U.S. Appl. No. 11/829,138, filed Jul. 27, 2007.

Rubenstein et al., Clinical Practice Guidelines for the Prevention and Treatment of Cancer Therapy—Induced Oral and Gastrointestinal Mucositis, *Cancer*, vol. 100(9) Suppl. pp. 2026-2046 (2004).

Wang et al., "Antioxidant and anti-inflammatory activities of anthocyanins and their aglycon, cyanidin, from tart cherries," *J. Nat. Prod.*, vol. 62, pp. 294-296 (1999).

Worthington et al., Interventions for preventing oral mucositis for patients with cancer receiving treatment, *Cochrane Database of Systemic Reviews*, Issue 2, p. 1-3 (2009).

(56) References Cited

OTHER PUBLICATIONS

Written Opinion of the International Search Authority dated Feb. 3, 2009 for PCT/IB2007/002147, filed Jul. 27, 2007.

* cited by examiner

METHODS FOR TREATING AND PREVENTING MUCOSITIS

RELATED APPLICATION

This application is a continuation of U.S. application Ser. No. 11/829,138, filed on Jul. 27, 2007 now abandoned, which is herein incorporated by reference in its entirety for all purposes.

FIELD OF THE INVENTION

Methods for treating and preventing mucositis, in particular mucositis following the administration of chemotherapy drugs or a combination of said drugs with radiotherapy, are disclosed herein. More specifically, disclosed herein is the administration of a therapeutically effective amount of at least one of an anthocyanoside, a proanthocyanidin, or an extract containing at least one of an anthocyanoside or a proanthocyanidin for the treatment or prevention of mucositis. The therapeutically effective amount of the anthocyanoside, proanthocyanidin or extract can be administered alone or in combination with a therapeutically effective amount of at least one of an anti-inflammatory agent, immunomodulating agent, analgesic, antimicrobial agent or antifungal agent. Also disclosed herein are pharmaceutical compositions for treating and preventing mucositis.

BACKGROUND

The first aim of oncology is the complete eradication of the tumor by any means, even when this leads to serious side effects; the motto primum non nocere ("first, do no harm") is not used as a guideline in the treatment of tumors, but has to be replaced with primum succerrere ("first, hasten to help"). Oncological treatment normally involves radical surgery, a targeted radiotherapy including photodynamic treatment, high doses of chemotherapy drugs, radiotherapy, and the maximum tolerated dose of cytokines when patients have serious side effects. In addition to these treatments, it is established practice to administer monoclonal antibodies for specific tumors in combination with chemotherapy, which has side effects similar to those reported for the combination of chemotherapy and radiotherapy. The challenge facing the medical profession is consequently to use all available means to maximize the therapeutic result.

However, current treatments are not sufficiently selective to target the tumor cell alone; chemotherapy also targets all actively proliferating tissues, creating problems in the tissues similar to those caused by radiotherapy. These treatments induce necrotic processes which lead to negative immune responses, and induce serious inflammatory processes.

One of the side effects of radiotherapy, and above all chemotherapy, is mucositis, which normally affects the gastroenteric tract, especially the mouth, esophagus, stomach, intestine and the vagina in women. The colon is involved in most cases, as are other accessible mucous membranes. Furthermore, the treatment of mucositis must be adjusted for each type of chemotherapy or anti-proliferation drug used. Mucositis may also affect the sex organs.

The drugs that mainly cause mucositis are anthracyclines, fluorouracyl, paclitaxel, actinomycin, mithramycin, etoposide, topotecan, amsacrine, methotrexate, hydroxyurea and combinations thereof with other chemotherapy drugs such as the platinum complexes, etc., which are the most common drugs used in oncological treatment.

Mucositis is a serious symptom, which adversely affects the patient's quality of life, as it makes eating difficult, and leads to infections that require the discontinuance of chemotherapy or the replacement of effective constituents of the mixtures, with a consequent reduction in the efficacy of treatment. The combination of chemotherapy and radiotherapy causes mucositis in 90% of patients. Mucositis is caused by immune reactions, which are still being researched, together with the direct effect of chemotherapy on actively proliferating tissues. As the mucous membranes are actively proliferating tissues, lesions that form during chemotherapy, due to thinning of the mucous layer, are normally followed by infections of bacterial, fungal and viral origin. In view of the genesis of mucositis, complete treatment generally requires systemic administration of antibiotics, antifungals or anti-inflammatory agents with immunostimulating properties, combined with topical treatments containing compounds that modulate wound-healing and prevent infection.

SUMMARY OF THE INVENTION

Described herein are methods of treating or preventing mucositis in a patient, e.g., a patient in need thereof, comprising administering to the patient a therapeutically effective amount of at least one of an anthocyanoside, a proanthocyanidin, or an extract, such as a plant extract, comprising at least one of an anthocyanoside or a proanthocyanidin. For instance, the methods can comprise administering therapeutically effective amounts of one or more of an anthocyanoside, a proanthocyanidin or such an extract, or various combinations of such compounds and extracts. As used herein, the term "anthocyanoside(s)" includes anthocyanosides, aglycones of anthocyanosides, i.e., anthocyanidins, as well as salts and derivatives thereof. Furthermore, as used herein, the term "anthocyanoside" is interchangeable and synonymous with the term "anthocyan." Also, as used herein, the term "aglycone" is interchangeable and synonymous with the term "aglycon." Moreover, as used herein, the term "proanthocyanidin" is interchangeable and synonymous with the term "procyanidin."

Also described herein are pharmaceutical compositions for treating or preventing mucositis, in which the compositions comprise (1) a therapeutically effective amount of at least one of an anthocyanoside, a proanthocyanidin, or an extract, such as a plant extract, comprising at least one of an anthocyanoside or a proanthocyanidin, and (2) a pharmaceutically acceptable excipient. For example, the compositions can comprise therapeutically effective amounts of one or more of an anthocyanoside, a proanthocyanidin or such an extract, or various combinations of such compounds and extracts.

Examples of anthocyanosides include without limitation glycosides of cyanidin, delphinidin, or pelargonidin, or aglycones of such glycosides. Examples of proanthocyanidins include without limitation proanthocyanidin A2 or proanthocyanidin B2. Examples of plant extracts comprising at least one of an anthocyanoside or a proanthocyanidin include without limitation extracts derived from *Vaccinium myrtillus*, *Vitis vinifera* or other plants containing such compounds. In some embodiments, the therapeutically effective amount of the anthocyanoside, proanthocyanidin or extract comprising at least one anthocyanoside or proanthocyanidin can be about 50 mg to about 500 mg per unit dose. In other embodiments, the therapeutically effective amount of the anthocyanoside, proanthocyanidin or extract comprising at least one anthocyanoside or proanthocyanidin can be about 3000 mg or less per day. Also, the therapeutically effective amount of the anthocyanoside, proanthocyanidin or extract comprising at least one anthocyanoside or proanthocyanidin can be administered to the patient by systemic administration, such as oral administration, or by topical administration.

In certain embodiments, the methods described herein can further comprise administering a therapeutically effective amount of at least one of an anti-inflammatory agent, immunomodulating agent, analgesic, antimicrobial agent or antifungal agent. Also, the compositions described herein can further comprise a therapeutically effective amount of at least one of such agents. The anti-inflammatory agent, immunomodulating agent or analgesic can comprise an andrographolide or a natural or synthetic analogue thereof, a lactone sesquiterpene or a natural or synthetic analogue thereof, a parthenolide or a natural or synthetic analogue thereof, a cynaropicrin or a natural or synthetic analogue thereof, or a isobutylamide of a polyunsaturated fatty acid, or a lipophilic extract of *Zanthoxylum bungeanum* or an extract of *Echinacea angustifolia*. In certain methods and compositions, the lipophilic extract of *Zanthoxylum bungeanum* or an extract of *Echinacea angustifolia* is present in amounts of about 0.02 mg to 0.05 mg per unit dose.

The antimicrobial agent or antifungal agent can be natural or synthetic. For example, the antimicrobial agent or antifungal agent can comprise miconazole; an antibiotic; a benzofuran; an isoquinoline alkaloid, such as a benzophenanthridine alkaloid or phenanthridine alkaloid; a sanguinarine or a natural or synthetic analogue thereof; chelerythrine or a natural or synthetic analogue thereof; chelidonine or a natural or synthetic analogue thereof; eupomatenoid or a natural or synthetic analogue thereof; or an extract, such as a plant extract, comprising any such compounds. Also, the antimicrobial agent or antifungal agent can comprise an extract of *Sanguinaria canadensis*, *Macleaya cordata* or *Macleaya microcarpa*. The therapeutically effective amount of the antimicrobial agent or the antifungal agent can be administered to the patient by systemic administration, such as oral administration, or by topical administration.

For instance, the method can comprising administering and the composition can comprise a tablet, such as a slow-dissolving tablet, or other pharmaceutical composition. The pharmaceutical composition can comprise an extract of *Vaccinium myrtillus*, and an isoquinoline alkaloid extracted from *Sanguinaria canadensis*, *Macleaya cordata* or *Macleaya microcarpa*. The pharmaceutical composition can further comprise a lipophilic extract of *Zanthoxylum bungeanum*.

The pharmaceutical composition can take on various forms. In some instances, it is in the form of a tablet, a capsule, a chewing gum, a liquid form, a vaginal gel or granulates. In some embodiments, the pharmaceutical composition is in the form of a tablet, such as a slow dissolving tablet, and the therapeutically effective amount of the anthocyanoside, proanthocyanidin or extract comprising at least one anthocyanoside or a proanthocyanidin is contained in the tablet in an amount of about 10 mg to about 200 mg per tablet. In another embodiment, the pharmaceutical composition is in the form of a tablet and the therapeutically effective amount of the antimicrobial agent or the antifungal agent is contained in the tablet in an amount of about 2 mg to about 10 mg per tablet.

Mucositis in various parts of the patient's body can be treated or prevented using the methods and compositions described herein. For instance, the mucositis can occur in a part of the patient's gastroenteric tract, such as the patient's mouth, esophagus, stomach, intestine, or colon. In other embodiments, the mucositis can occur in a sex organ, such as the vagina, or the skin. In certain cases involving a sex organ, a therapeutically effective amount of a benzophenanthridine alkaloid, a benzofuran or an analogue thereof, a hyperforin or an analogue thereof, or a fluoroglucinol or an analogue thereof can be administered to the patient or included in the compositions.

In some embodiments, the patient has a cancer. Moreover, the mucositis can occur in connection with the administration of a chemotherapy or a radiotherapy to the patient, such as the administration of an anthracycline, fluorouracyl, paclitaxel, actinomycin, mithramycin, etoposide, topotecan, amsacrine, methotrexate, hydroxyurea or a platinum complex. The therapeutically effective amount of the anthocyanoside, proanthocyanidin or extract comprising at least one of an anthocyanoside or a proanthocyanidin can be administered to the patient before, after or while the patient receives a chemotherapy.

DETAILED DESCRIPTION

Anthocyanosides and proanthocyanidins are substances with different action mechanisms partly associated with their chemical nature. These substances are potent antioxidants, stimulators of fibroblast proliferation and mucous production at the gastric level, potent inhibitors of proteases, (especially β-glucuronidase, hyaluronidase and collagenase), and potent wound-healing agents. A special feature is their effect on capillary fragility and permeability, which often leads to significant topical anti-inflammatory activity. Anthocyanosides and proanthocyanidins as well as compositions comprising such compounds are described in International Publication No. WO 2006/063716A1 (PCT application no. PCT/EP2005/013047), which is incorporated herein in its entirety for all purposes. The most appropriate polyphenol agents will be selected, depending on the area affected by mucositis. As anthocyanosides and anthocyanidins, have a strong red coloring due to their chemical nature, they will be used for treatment of the gastroenteric tract. For treatment of sex organs or exposed skin areas, anthocyanosides will be replaced with proanthocyanidins, which are not colored and equally active for these purposes.

Anthocyanosides, especially glycosides of cyanidin or delphinidin or aglycones of such glycosides, which are abundantly present, for example, in the extracts of *Vaccinium myrtillus* and other species, have demonstrated significant preventive and curative antiulcer activity in the rat, when administered orally, in various models of experimental gastric ulcers (pylorus-ligature, reserpine, phenylbutazone, restraint, and acetic acid) without affecting gastric secretion, and increasing the mucous layer as can be demonstrated histologically. Again in the rat, these compounds protect the gastric mucosa against lesions induced by aspirin, a finding which has also been confirmed in man by measuring occult blood in the stool.

When administered by the gastric route, the compounds inhibit the reduction of transmucosal potential, and increase $H^+$ backscattering induced by salicylates. All these parameters suggest that gastroprotective activity is associated with the efficiency of the mucosal barrier. In volunteers, the administration of cyanidin significantly increased the secretion of $PGE_2$ compared with the controls, which helps to explain the gastro-protective effect of anthocyanosides. The RNA/DNA ratio and protein synthesis also increase, as does mucus secretion. The most marked phenomenon relates to mucus production and its storage after formation due to the inhibitory effect on metalloproteases, such as hyaluronidase, collagenase and glucuronidase. These actions can be documented by direct topical and systemic action. Both the anthocyanosides and the proanthocyanidins disclosed herein have a marked wound-healing activity, which is useful to protect against tissue damage.

It is therefore very important to use these products to treat patients who undergo chemotherapy with drugs which are well known to cause mucositis.

As bacterial and/or fungal infections are particularly frequent in mucositis, a treatment, such as a topical treatment, with substances that inhibit the growth of both bacteria and fungi is particularly important. The antimicrobial or antifungal agents or substances chosen for this purpose include isoquinoline alkaloids, such as benzophenanthridine alkaloids or phenanthridine alkaloids, sanguinarine, chelerythrine and chelidonine, which inhibit the growth of Gram+ and Gram− bacteria, and numerous strains of Candida and other pathogenic fungi, at nanomolar concentrations. Synthetic antifungals such as miconazole or antifungal antibiotics, and benzofurans such as eupomatenoid and its natural or synthetic analogues, can be used in combination in different ways. The advantage of the isoquinoline alkaloids, such as benzophenanthridine alkaloids or phenanthridine alkaloids, is that these compounds are only absorbed to a small extent by oral administration, are very potent antimicrobials, and possess a strong local analgesic action. In some formulations for the treatment of mucositis induced by chemotherapy drugs, it can be useful for some forms to combine isobutylamides of polyunsaturated fatty acids which possess an agonistic effect on the cannabinoid CB1 and CB2 receptors and an anti-inflammatory and analgesic action.

Treatment with the formulations disclosed herein has the unusual feature that all the constituents of the combination are absorbed to a negligible extent on oral administration, so they can be administered on a preventive basis, before chemotherapy begins, or simultaneously, continuing the treatment between cycles to reduce the risk of mucositis. If these components are absorbed, they have an angiogenetic activity as reported in *Free Radical Research*, 36, 1023-31, 2002, inhibiting VEGF expression. Systemic treatment with anti-inflammatory immunostimulants involves the use of andrographolide and its natural or synthetic analogues, or the use of lactone sesquiterpenes such as parthenolide, cynaropicrin or their natural or synthetic analogues. These compounds inhibit inflammatory processes by acting on TNF-α and NF-kB, and stimulate immunological reactivity.

In addition to alkaloid antimicrobial agents, natural or synthetic benzofurans were chosen which present complementary activity to those agents, acting with different mechanisms.

The compositions disclosed herein prevent the formation of purulent plaques in the oral cavity variously infected by saprophytes, avoiding the use of antibiotics, and at the same time reducing the length of the infection. The pharmaceutical compositions to be used are mainly formulated as tablets which dissolve slowly in the oral cavity, or as chewing gums which allow slow release of the active constituents. These compositions are mainly used in preventive treatments, but also curatively, and for oral hygiene. According to a preferred aspect, the compositions disclosed herein will also contain essential oils to increase their approval rating in terms of freshness of the oral cavity.

In human pharmacological treatment, the doses which have proved effective when administered in a suitable formulation range between 10 and 200 mg per tablet for anthocyanosides, proanthocyanidins or extracts comprising at least one anthocyanoside or proanthocyanidin, and a concentration of an isoquinoline alkaloid, such as a benzophenanthridine alkaloid or phenanthridine alkaloid, ranging between 2 and 10 mg per tablet, or between 0.05 and 0.2% when administered in liquid forms for gargling, etc. Also, the methods can comprise administering or the compositions can comprise extracts containing an anthocyanoside or a proanthocyanidin in amounts of about 20 mg to about 80 mg per unit dose. In some embodiments, the methods comprise administering or the compositions comprise extracts containing isoquinoline alkaloids in amounts of about 2 mg to about 20 mg per dose.

In particular, the compositions disclosed herein exert not only a preventive but a therapeutic effect, especially as regards the duration of the pathological form.

The compositions also includes pediatric formulations, such as slow-dissolving gum or candy forms compatible with the stability of the active constituents. Tablets, capsules and dispersible granulates or oral liquid forms which promote close contact between the active constituents and the walls of the gastroenteric tract will be used to treat gastric and colorectal mucositis. The formulations for this specific indication cannot contain antimicrobial agents, but will always preferably contain anti-inflammatory and immunomodulating agents. The treatment will preferably be performed with anthocyanosides of *Vaccinium myrtillus* or *Vitis vinifera* at doses ranging between 50 and 500 mg per unit dose, or with cyanidin, delphinidin or pelargonidin at similar doses, with daily treatment of up to 3000 mg.

Proanthocyanidins, such as proanthocyanidin A2 or B2, will be used to treat mucositis of the sex organs, especially the vagina, preferably in combination with isoquinoline alkaloids, such as benzophenanthridine alkaloids or phenanthridine alkaloids, or benzofuran such as eupomatenoid and its analogues, or with terpenes such as hyperforin and its analogues and fluoroglucinols extracted from *Myrtus communis* or *Humulus luppulus*. These formulations include vaginal pessaries, foams, gels or creams, depending on the tolerability of the preparations to the damaged mucous membranes. These compositions will therefore be prepared in accordance with conventional methods, like those described in "Remington's Pharmaceutical Handbook", Mack Publishing Co., N.Y., USA, together with suitable excipients.

The following illustrative examples are set forth to assist in understanding the methods and compositions described herein and do not limit the claimed methods and compositions.

EXAMPLES

Example I

| | Tablets - composition per tablet | |
|---|---|---|
| 1. | *Vaccinium myrtillus* extract | 100.0 mg |
| 2. | *Sanguinaria canadensis* alkaloids | 6.0 mg |
| 3. | Mannitol | 688.0 mg |
| 4. | Xylitol | 600.0 mg |
| 5. | Glyceryl behenate | 30.0 mg |
| 6. | Anhydrous citric acid | 20.0 mg |
| 7. | Silicon dioxide | 15.0 mg |
| 8. | Liquorice flavoring | 15.0 mg |
| 9. | Mint flavoring | 10.0 mg |

-continued

| Tablets - composition per tablet | | |
|---|---|---|
| 10. | Magnesium stearate | 7.0 mg |
| 11. | Menthol crystals | 5.0 mg |
| 12. | Potassium acesulfame | 4.0 mg |

The menthol crystals were ground to a fine powder and mixed with all the other constituents of the formulation, using a suitable mixer (e.g. a V-mixer). The mixture of powders was then compressed with a tablet press, equipped with punches of suitable dimensions, to give 1500 mg tablets.

Example II

| Tablets - composition per tablet | | |
|---|---|---|
| 1. | Cyanidin chloride | 100.00 mg |
| 2. | *Sanguinaria canadensis* alkaloids | 4.00 mg |
| 3. | Lipophilic extract of *Zanthoxylum bungeanum* | 0.25 mg |
| 4. | Mannitol | 442.75 mg |
| 5. | Xylitol | 300.00 mg |
| 6. | Lactose | 100.00 mg |
| 7. | Glycerol palmitostearate | 50.00 mg |
| 8. | Methylcellulose | 40.00 mg |
| 9. | Soft fruit flavoring | 30.00 mg |
| 10. | Hydrogenated vegetable oils | 10.00 mg |
| 11. | Liquorice flavoring | 10.00 mg |
| 12. | Mint flavoring | 6.00 mg |
| 13. | Anhydrous citric acid | 5.00 mg |
| 14. | Potassium acesulfame | 2.00 mg |

Ximenoil isobutylamide, adsorbed on a small amount of mannitol, was mixed with cyanidin chloride, *Sanguinaria canadensis* alkaloids, the remaining mannitol, xylitol, lactose, flavorings and anhydrous citric acid. The mixture of powders was then mixed with a hydroalcoholic solution of methylcellulose (wet granulation). The mixture obtained was passed through a 10 mesh screen, dried in the stove, sieved through a 20 mesh screen and finally mixed with the other components of the formulation using a suitable mixer. The mixture of powders was compressed with a tablet press, equipped with punches of suitable dimensions, to obtain 1100 mg tablets.

Example III

| 1000 mg Tablets | | |
|---|---|---|
| 1. | *Vaccinium myrtillus* alcoholic extract | 40.0 mg |
| 2. | sanguiritrinum | 2.0 mg |
| 3. | *Zanthoxylum bungeanum* extracted purified | 0.025 mg |
| 4. | glyceryl behanate | 30.0 mg |
| 5. | Anhydrous citric acid | 20.0 mg |
| 6. | powdered liquorice juice | 80.0 mg |
| 7. | xylitol | 628.975 mg |
| 8. | Mannitol | 700.0 mg |
| 9. | silicon dioxide | 15.0 mg |
| 10. | peppermint flavoring | 10.0 mg |
| 11. | magnesium stearate | 7.5 mg |
| 12. | potassium acesulfame | 4.0 mg |
| 13. | menthol | 5.0 mg |
| 14. | hydroxypropylcellulose | 0.004 mg |

The menthol crystals were grounded to obtain a fine powder. *Zanthoxylum bungeanum* extract was adsorbed on a small amount of mannitol and mixed with the remaining components of the formulation along with the remaining portion of the mannitol and with the ground menthol. The mixture was passed through a 20 mesh screen and compressed with punches of suitable size to obtain 1000 mg tablets. Hydroxypropylcellulose was dissolved in purified water and sprayed on the tablets.

Example IV

| 1000 mg Tablets | | |
|---|---|---|
| 1. | *Vaccinium myrtillus* alcoholic extract | 40.0 mg |
| 2. | *Sanguinaria canadensis* alcoholic extract | 2.0 mg |
| 3. | *Zanthoxylum bungeanum* extracted purified | 0.025 mg |
| 4. | Soy lecithin | 30.0 mg |
| 5. | Anhydrous citric acid | 5.0 mg |
| 6. | L-Cysteine | 5.0 mg |
| 7. | Lactose | 200.0 mg |
| 8. | Mannitol | 552.475 mg |
| 9. | Methylcellulose | 40.0 mg |
| 10. | Glycerol palmitostearate | 50.0 mg |
| 11. | Berry flavor | 40.0 mg |
| 12. | potassium acesulfame | 0.5 mg |
| 13. | Talc | 10.0 mg |
| 14. | Sodium bicarbonate | 25.0 mg |

*Zanthoxylum bungeanum* extract was adsorbed on a small amount of mannitol and mixed with the remaining components of the formulation along with the remaining portion of the mannitol. The mixture was passed through a 20 mesh screen and compressed with punches of suitable size to obtain 1000 mg tablets.

Example V

| 1000 mg Tablets | | |
|---|---|---|
| 1. | *Vitis vinifera* alcoholic extract | 80.0 mg |
| 2. | *Sanguinaria canadensis* alcoholic extract | 2.0 mg |
| 3. | *Zanthoxylum bungeanum* extracted purified | 0.025 mg |
| 4. | Soy lecithin | 30.0 mg |
| 5. | Anhydrous citric acid | 5.0 mg |
| 6. | L-Cysteine | 5.0 mg |
| 7. | Lactose | 200.0 mg |
| 8. | Mannitol | 512.475 mg |
| 9. | Methylcellulose | 40.0 mg |
| 10. | Glycerol palmitostearate | 50.0 mg |
| 11. | Berry flavors | 40.0 mg |
| 12. | potassium acesulfame | 0.5 mg |
| 13. | Talc | 10.0 mg |
| 14. | Sodium bicarbonate | 25.0 mg |

*Zanthoxylum bungeanum* extract was adsorbed on a small amount of mannitol and mixed with the remaining components of the formulation along with the remaining portion of the mannitol. The mixture was passed through a 20 mesh screen and compressed with punches of suitable size to obtain 1000 mg tablets.

Example VI

| 1000 mg Tablets | | |
|---|---|---|
| 1. | *Vaccinium myrtillus* alcoholic extract | 40.0 mg |
| 2. | *Sanguinaria canadensis* alcoholic extract | 2.0 mg |
| 3. | *Echinacea angustifolia* lipophilic extract | 5.0 mg |
| 4. | Soy lecithin | 30.0 mg |

| 1000 mg Tablets | | |
|---|---|---|
| 5. | Anhydrous citric acid | 5.0 mg |
| 6. | L-Cysteine | 5.0 mg |
| 7. | Lactose | 200.0 mg |
| 8. | Mannitol | 547.5 mg |
| 9. | Methylcellulose | 40.0 mg |
| 10. | Glycerol palmitostearate | 50.0 mg |
| 11. | Berry flavors | 40.0 mg |
| 12. | potassium acesulfame | 0.5 mg |
| 13. | Talc | 10.0 mg |
| 14. | Sodium bicarbonate | 25.0 mg |

*Echinacea angustifolia* extract was adsorbed on a small amount of mannitol and mixed with the remaining components of the formulation along with the remaining portion of the mannitol. The mixture was passed through a 20 mesh screen and compressed with punches of suitable size to obtain 1000 mg tablets.

Example VII

| 1000 mg Tablets | | |
|---|---|---|
| 1. | *Vitis vinifera* alcoholic extract | 80.0 mg |
| 2. | *Sanguinaria canadensis* alcoholic extract | 2.0 mg |
| 3. | *Echinacea angustifolia* lipophilic extract | 5.0 mg |
| 4. | Soy lecithin | 30.0 mg |
| 5. | Anhydrous citric acid | 5.0 mg |
| 6. | L-Cysteine | 5.0 mg |
| 7. | Lactose | 200.0 mg |
| 8. | Mannitol | 507.5 mg |
| 9. | Methylcellulose | 40.0 mg |
| 10. | Glycerol palmitostearate | 50.0 mg |
| 11. | Berry flavors | 40.0 mg |
| 12. | potassium acesulfame | 0.5 mg |
| 13. | Talc | 10.0 mg |
| 14. | Sodium bicarbonate | 25.0 mg |

*Echinacea angustifolia* extract was adsorbed on a small amount of mannitol and mixed with the remaining components of the formulation along with the remaining portion of the mannitol. The mixture was passed through a 20 mesh screen and compressed with punches of suitable size to obtain 1000 mg tablets.

Example VIII

| Hard Gelatin Capsules - composition per capsule | |
|---|---|
| Cyanidin | 250 mg |
| Lactose | 100 mg |
| Microcrystalline cellulose | 100 mg |
| Cross-linked sodium carboxymethylcellulose | 45 mg |
| Colloidal silicon dioxide | 5 mg |

The powders were mixed in a suitable mixer, and the mixture obtained was used to fill hard gelatin capsules at an amount of 500 mg/capsule.

Example IX

| Hard Gelatin Capsules - composition per capsule | | |
|---|---|---|
| 1. | Cyanidin | 200 mg |
| 2. | Andrographolide | 70 mg |
| 3. | Lactose | 100 mg |
| 4. | Microcrystalline cellulose | 100 mg |
| 5. | Cross-linked sodium carboxymethylcellulose | 40 mg |
| 6. | Colloidal silicon dioxide | 5 mg |
| 7. | Magnesium stearate | 5 mg |

The preparation method for Example IX was similar to that described for Example VIII.

Example X

| Water-Dispersible Granulate | | |
|---|---|---|
| 1. | Alcoholic extract of *Vaccinium myrtillus* | 100.0 mg |
| 2. | Chelidonine | 3.0 mg |
| 3. | Mannitol | 1200.0 mg |
| 4. | Maltodextrin | 913.0 mg |
| 5. | Guar gum | 120.0 mg |
| 6. | Hydroxypropylcellulose | 20.0 mg |
| 7. | Strawberry flavoring | 15.0 mg |
| 8. | Anhydrous citric acid | 15.0 mg |
| 9. | Aspartame | 10.0 mg |
| 10. | Neohesperidine | 4.0 mg |

Alcoholic extract of *Vaccinium myrtillus*, chelidonine, mannitol, maltodextrin, guar gum, anhydrous citric acid, aspartame and neohesperidine were mixed with a suitable mixer (e.g. a V-mixer). The mixture of powders thus obtained was mixed with an alcoholic solution of hydroxypropylcellulose (wet granulation). The mixture obtained was granulated on a 10 mesh screen, dried in a stove under vacuum, sieved through a 20 mesh screen and mixed with the flavoring. Sachets were filled with the granulate thus obtained, in the amount of 2400 mg/sachet Example XI

| Vaginal Gel | | |
|---|---|---|
| 1. | Proanthocyanidin A2 | 1.0 g |
| 2. | *Sanguinaria canadensis* alkaloids | 0.003 g |
| 3. | Propylene glycol | 10.0 g |
| 4. | Ethoxydiglycol | 10.0 g |
| 5. | Softigen 767 | 10.0 g |
| 6. | Polysorbate 80 | 4.0 g |
| 7. | Carbomer | 2.0 g |
| 8. | Triethanolamine 20% solution | 2.0 g |
| 9. | Methyl paraben | 0.2 g |
| 10. | Propyl paraben | 0.1 g |
| 11. | Purified water q.s for | 100.0 g |

Proanthocyanidin A2 and *Sanguinaria canadensis* alkaloids were added to a mixture of propylene glycol and ethoxydiglycol. The solution was heated, and Softigen 767 was added under agitation. The solution was left to cool, and Polysorbate 80, methyl- and propyl paraben were added. Purified water was added to the solution, and the carbomer was dispersed under intense agitation. The solution was deareated under vacuum, and gelled under agitation with 20% triethanolamine solution.

Example XII

| | Vaginal Gel | |
|---|---|---|
| 1. | Proanthocyanidin A2 | 1.0 g |
| 2. | Sanguinarine | 0.002 g |
| 3. | Propylene glycol | 10.0 g |
| 4. | Ethoxydiglycol | 10.0 g |
| 5. | Softigen 767 | 10.0 g |
| 6. | Polysorbate 80 | 4.0 g |
| 7. | Carbomer | 2.0 g |
| 8. | Triethanolamine 20% solution | 2.0 g |
| 9. | Methyl paraben | 0.2 g |
| 10. | Propyl paraben | 0.1 g |
| 11. | Purified water q.s for | 100.0 g |

Proanthocyanidin A2 and sanguinarine were added to a mixture of propylene glycol and ethoxydiglycol. The solution was heated, and Softigen 767 was added under agitation. The solution was left to cool, and Polysorbate 80, methyl- and propyl paraben were added. Purified water was added to the solution, and the carbomer was dispersed under intense agitation. The solution was deareated under vacuum, and gelled under agitation with 20% triethanolamine solution.

Example XIII

| | Vaginal gel | |
|---|---|---|
| 1. | Proanthocyanidin A2 | 1.0 g |
| 2. | Eupomatenoid 6 | 0.012 g |
| 3. | Propylene glycol | 10.0 g |
| 4. | Ethoxydiglycol | 10.0 g |
| 5. | Softigen 767 | 10.0 g |
| 6. | Polysorbate 80 | 4.0 g |
| 7. | Carbomer | 2.0 g |
| 8. | Triethanolamine 20% solution | 2.0 g |
| 9. | Methyl paraben | 0.2 g |
| 10. | Propyl paraben | 0.1 g |
| 11. | Purified water q.s for | 100.0 g |

Proanthocyanidin A2 and eupomatenoid 6 were added to a mixture of propylene glycol and ethoxydiglycol. The solution was heated, and Softigen 767 was added under agitation. The solution was left to cool, and Polysorbate 80, methyl- and propyl paraben were added. Purified water was added to the solution, and the carbomer was dispersed under intense agitation. The solution was deareated under vacuum, and gelled under agitation with 20% triethanolamine solution.

The description contained herein is for purposes of illustration and not for purposes of limitation. The methods and compositions described herein can comprise any feature described herein either alone or in combination with any other feature(s) described herein. Changes and modifications may be made to the embodiments of the description. Furthermore, obvious changes, modifications or variations will occur to those skilled in the art. Also, all references cited above are incorporated herein, in their entirety, for all purposes related to this disclosure.

What is claimed is:

1. A method for the treatment of mucositis in a patient comprising administering to the patient a therapeutically effective composition for the treatment of mucositis, wherein the composition comprises: (1) one or more extracts of *Vaccinium myrtillus*; (2) one or more extracts of *Macleaya cordata*; and (3) one or more extracts of *Echinacea angustifolia*, wherein the mucositis occurs in connection with the administration of chemotherapy and/or radiotherapy to the patient.

2. The method of claim 1, wherein the extracts of *Vaccinium myrtillus* comprise one or more anthocyanosides.

3. The method of claim 1, wherein the extracts of *Macleaya cordata* comprise one or more isoquinoline alkaloids.

4. The method of claim 1, wherein the extracts of *Echinacea angustifolia* are lipophilic.

5. The method of claim 1, wherein the composition is administered to the patient by systemic administration.

6. The method of claim 5, wherein the systemic administration comprises oral administration.

7. The method of claim 1, wherein the composition is administered to the patient by topical administration.

8. The method of claim 1, wherein the mucositis occurs in the patient's mouth.

9. The method of claim 1, wherein the composition is administered to the patient before the patient receives chemotherapy and/or radiotherapy.

10. The method of claim 1, wherein the composition is administered to the patient while the patient receives chemotherapy and/or radiotherapy.

11. The method of claim 1, wherein the composition is administered to the patient after the patient receives chemotherapy and/or radiotherapy.

* * * * *